United States Patent

Lafon

Patent Number: 5,446,060
Date of Patent: Aug. 29, 1995

[54] AMINOALKYL THIENYL KETONE DERIVATIVES AND THEIR USE AS PERIPHERAL VASODILATORS

[75] Inventor: Louis Lafon, Paris, France

[73] Assignee: Laboratoire L. Lafon, Maisons Alfort, France

[21] Appl. No.: 183,904

[22] Filed: Jan. 21, 1994

Related U.S. Application Data

[63] Continuation of Ser. No. 802,820, Dec. 6, 1991, abandoned.

[30] Foreign Application Priority Data

Dec. 12, 1990 [FR] France .................. 90 15591

[51] Int. Cl.$^6$ .............. C07D 409/06; A61K 31/38; A61K 31/40
[52] U.S. Cl. .............. 514/422; 548/315.1; 548/527; 540/596; 544/146; 544/359; 544/374; 546/212; 514/212; 514/236.8; 514/258; 514/326; 514/397
[58] Field of Search ............... 540/596; 544/146, 359, 544/374; 546/212; 548/315.1, 527; 514/422, 397, 212, 258, 236.8

[56] References Cited

U.S. PATENT DOCUMENTS

| | | | |
|---|---|---|---|
| 3,189,600 | 6/1965 | Huebner | 544/146 X |
| 3,372,162 | 3/1968 | Prsson et al. | 548/527 X |
| 3,417,087 | 12/1968 | Campaigne et al. | 544/146 |
| 4,009,184 | 2/1977 | Kaupmann et al. | 540/596 X |
| 4,079,140 | 3/1978 | Robba et al. | 540/596 X |
| 4,186,136 | 1/1980 | Robba et al. | 540/596 |
| 4,299,769 | 11/1981 | McEvoy et al. | 544/146 X |
| 5,061,704 | 10/1991 | Wierzbicki et al. | 544/146 X |

FOREIGN PATENT DOCUMENTS

| | | | |
|---|---|---|---|
| 0193875 | 9/1986 | European Pat. Off. | 540/596 |
| 3414 | 7/1965 | France | 544/374 |
| 2134218 | 12/1972 | France | 544/374 |
| 2184503 | 12/1973 | France | 546/212 |
| 2453172 | 10/1980 | France | 544/374 |
| 2552151 | 5/1976 | Germany | 544/374 |
| 60-28973 | 2/1985 | Japan | 544/146 |

*Primary Examiner*—Floyd D. Higel
*Attorney, Agent, or Firm*—Jacobson, Price, Holman & Stern

[57] ABSTRACT

The present invention relates to compounds of formula:

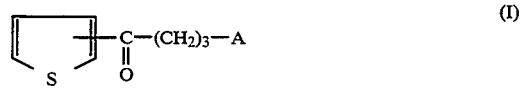

in which A is selected from pyrrolidino, piperidino, morpholino, 1-imidazolyl, hexamethylenimino and 1-piperazinyl groups, these groups being unsubstituted or it being possible for them to contain 1 or 2 substituents selected from $C_1$-$C_3$ alkyl and $C_1$-$C_3$ hydroxyalkyl groups, and the addition salts of these compounds with pharmaceutically acceptable acids.

These compounds are usable in therapy as peripheral vasodilators.

8 Claims, No Drawings

AMINOALKYL THIENYL KETONE DERIVATIVES AND THEIR USE AS PERIPHERAL VASODILATORS

This application is a continuation of U.S. application Ser. No. 07/802,820 filed Dec. 6, 1991, now abandoned.

The present invention relates to new aminoalkyl ketone derivatives, to a process for preparing them and to their use in therapy, in particular as peripheral vasodilators.

In FR-A-2,134,218, aminoalkyl ketone derivatives having peripheral vasodilator activity, and in particular buflomedil, have been described.

The present invention is directed towards the provision of new compounds which not only have peripheral vasodilator activity, but also have advantageous activity with respect to metabolism.

The subject of the present invention is thus compounds of formula

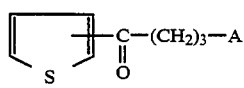   (I)

in which A is selected from pyrrolidino, piperidino, morpholino, 1-imidazolyl, hexamethylenimino and 1-piperazinyl groups, these groups being unsubstituted or it being possible for them to contain 1 or 2 substituents selected from $C_1$-$C_3$ alkyl and $C_1$-$C_3$ hydroxyalkyl groups, and the addition salts of these compounds with pharmaceutically acceptable acids.

As examples of groups A, pyrrolidino, 2,4-dimethylpyrrolidino, 2,5-dimethylpyrrolidino, piperidino, 3-methylpiperidino, 3-(hydroxymethyl)piperidino, morpholino, 1-imidazolyl, hexamethylenimino and N-methylpiperazino groups may be mentioned.

The "addition salts with pharmaceutically acceptable acids" denote the salts which give the biological properties of the free bases without having an adverse effect. These salts can be, in particular, those formed with inorganic acids such as hydrochloric acid, hydrobromic acid, sulphuric acid, nitric acid and phosphoric acid, acid salts of metals, such as disodium orthophosphate and monopotassium sulphate, and organic acids such as formic acid, acetic acid, propionic acid, glycolic acid, oxalic acid, fumaric acid, maleic acid, citric acid, malonic acid, methanesulphonic acid, lactic acid, succinic acid and tartaric acid.

The compounds according to the present invention may be prepared by the condensation of a chlorinated derivative of formula:

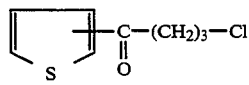   (II)

with a cyclic amine of formula:

HA   (III)

A having the meaning given above.

This reaction may be performed in the solvents customarily used for condensation reactions.

As a variant, the compounds according to the invention may be prepared by the reaction of a nitrile of formula:

   (IV)

with a lithium derivative of 2- or 3-bromothiophene, followed by hydrolysis.

This reaction may be carried out under the conventional conditions for using lithium derivatives.

The salts may be obtained in a conventional manner by reacting a compound of formula I with a pharmaceutically acceptable acid in a suitable solvent.

The examples which follow illustrate the preparation of the compounds according to the invention.

EXAMPLE 1

Preparation of 4-pyrrolidino-1-(2-thienyl)butanone hydrochloride (CRL 41687).

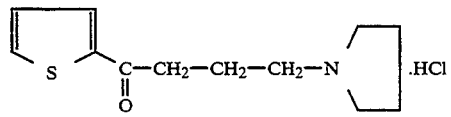

18.85 g (0.10 mol) of 4-chloro-1-(2-thienyl)butanone are run, over a period of 30 min, into a solution, maintained at 100° C., of 18.5 ml (0.22 mol) of pyrrolidine in 35 ml of toluene, and the mixture is heated to reflux for 2 hours. The reaction medium is diluted with ethyl ether and the mixture is washed with water. The organic phase is extracted with 2N hydrochloric acid solution which, after alkalinisation with sodium hydroxide, is in turn extracted with ethyl ether. The organic phase is dried over dry sodium sulphate and treated with a solution of hydrogen chloride in isopropanol.

The precipitate obtained is purified by two successive crystallisations with CXA charcoal treatment in isopropanol and absolute ethanol, to give 11.1 g of a slightly grey powder which is soluble in water to a concentration of 20%.

M.p.$_{inst.}$ (Kofler)=177° C.

Yield=46.3%.

EXAMPLE 2

Preparation of 4-piperidino-1-(2-thienyl)butanone hydrochloride (CRL 41696).

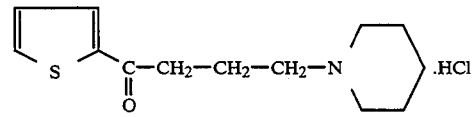

18.9 g (0.10 mol) of 4-chloro-1-(2-thienyl)butanone are run, over a period of 30 min, into a solution under reflux of 18.7 g (0.22 mol) of piperidine in 35 ml of toluene, and the heating is maintained for 2 hours. The reaction medium is diluted with ethyl ether and the mixture is washed with water. The organic phase is extracted with dilute hydrochloric acid solution and the aqueous phase alkalinised with sodium hydroxide. The aqueous phase is extracted with ethyl ether and, after drying over dry sodium sulphate, the organic phase is treated with a solution of hydrogen chloride in isopropanol.

EXAMPLE 3

Preparation of 4-(3-methylpiperidino)-1-(2-thienyl)-butanone hydrochloride (CRL 41686).

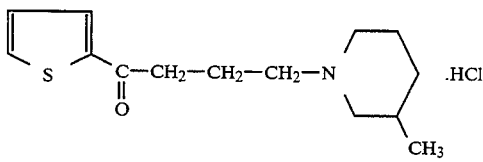

18.85 g (0.10 mol) of 4-chloro-1-(2-thienyl)butanone are run, over a period of 30 min, into a solution, maintained at 100° C., of 21.8 g (0.22 mol) of 3-methylpiperidine in 35 ml of toluene, and the mixture is heated to reflux for 2 hours. The reaction medium is diluted with ethyl ether and the mixture is washed with water. The organic phase is extracted with dilute hydrochloric acid solution which, after alkalinisation with sodium hydroxide, is in turn extracted with ethyl ether. The organic phase is dried over dry sodium sulphate and treated with a solution of hydrogen chloride in isopropanol.

The precipitate obtained is purified by a crystallisation in isopropanol, to give 18 g of a white powder which is soluble in water to a concentration of 20%.

M.p.$_{inst.}$ (Kofler) = 164° C.
Yield = 62.6%.

EXAMPLE 4

Preparation of 4-morpholino-1-(2-thienyl)butanone hydrochloride (CRL 41698).

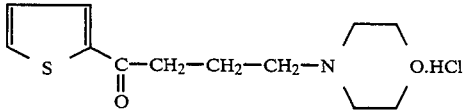

18.9 g (0.20 mol) of 4-chloro-1-(2-thienyl)butanone are run, over a period of 15 min, into a solution under reflux of 19.2 g (0.22 mol) of morpholine in 35 ml of toluene, and the heating is continued for 2 hours. The reaction medium is diluted with ethyl ether and the mixture is washed with water. The organic phase is extracted with dilute hydrochloric acid solution and the aqueous phase alkalinised with sodium hydroxide. The aqueous phase is extracted with ethyl ether and, after drying over dry sodium sulphate, the organic phase is treated with a solution of hydrogen chloride in isopropanol.

The precipitate obtained on filtration is purified by a crystallisation in methanol, to give 12.7 g of a water-soluble, beige powder.

M.P.$_{inst.}$ (Kofler) = 210° C.
Yield = 46.1%.

EXAMPLE 5

Preparation of 4-[3-(hydroxymethyl)piperidino]-1-(2-thienyl) butanone hydrochloride (CRL 41697).

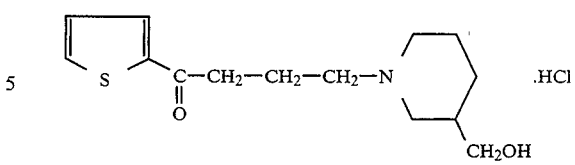

28.3 g (0.15 mol) of 4-chloro-1-(2-thienyl)butanone are run, over a period of 30 min, into a solution under reflux of 38 g (0.33 mol) of 3-piperidylmethanol in 55 ml of toluene, and the heating is maintained for 2 h 30 min. The reaction medium is diluted with ethyl acetate and the mixture is washed with water. The organic phase is extracted with dilute hydrochloric acid solution and the aqueous phase alkalinised with sodium hydroxide. The aqueous phase is extracted with ethyl acetate and, after drying over dry sodium sulphate, the organic phase is treated with a solution of hydrogen chloride in isopropanol.

The precipitate obtained on filtration is purified by a crystallisation in ethanol, to give 26 g of a water-soluble, slightly grey powder.

M.P.$_{inst.}$ (Kofler) = 160° C.
Yield = 57.1%.

EXAMPLE 6

Preparation of 4-(1-imidazolyl)-1-(2-thienyl)butanone hydrochloride (CRL 41703).

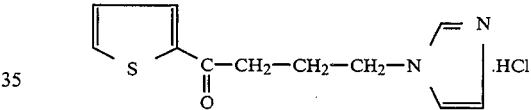

18.9 g (0.10 mol) of 4-chloro-1-(2-thienyl)butanone are run into a solution, maintained at about 90° C., of 15 g (0.22 mol) of imidazole in 35 ml of toluene, and the mixture is heated to reflux for 4 hours. The reaction medium is diluted with ethyl acetate and the mixture is washed with water and extracted with dilute hydrochloric acid solution. The aqueous phase is alkalinised with sodium hydroxide and extracted with ethyl acetate, which is dried over dry sodium sulphate. The solution is treated with a solution of hydrogen chloride in ethanol, and the insoluble matter purified by a wash in acetone, to give 6 g of a water-soluble, beige powder.

M.P.$_{inst.}$ (Kofler) = 132° C.
Yield = 23.4%.

EXAMPLE 7

Preparation of 4-hexamethylenimino-1-(2-thienyl)-butanone hydrochloride (CRL 41683).

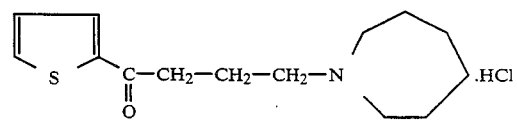

28.3 g (0.15 mol) of 4-chloro-1-(2-thienyl)butanone are run, over a period of 30 min, into a solution, maintained at 100° C., of 32.7 g (0.33 mol) of hexamethylenimine in 50 ml of toluene. Refluxing is continued for 3 hours, the reaction medium is diluted with 150 ml of ethyl ether, the insoluble matter is removed by filtration and the filtrate is extracted with dilute hydrochloric acid solution. The aqueous phase is alkalinised with concentrated sodium hydroxide and is in turn extracted with ethyl ether. After drying of the organic phase over dry sodium sulphate, the latter phase is treated with a solution of hydrogen chloride in isopropanol.

The precipitate is isolated by filtration and then purified by a crystallisation with CXA charcoal treatment in absolute ethanol, to give 33.1 g of a watersoluble, beige powder.

M.p.$_{inst.}$ (Kofler)=181° C.
Yield=76.75%.

EXAMPLE 8

Preparation of 4-pyrrolidino-1-(3-thienyl)butanone hydrochloride (CL 41724).

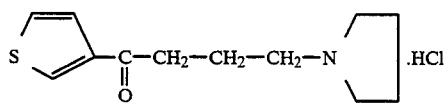

A solution of 16.3 g (0.10 mol) of 3-bromothiophene in 50 ml of ethyl ether is run, over a period of 10 min, into a solution, under a nitrogen atmosphere and maintained at −70° C., of 69 ml (0.11 mol) of a 1.6M hexane solution of butyllithium diluted in 150 ml of ethyl ether.

While the temperature is maintained at −50° C., 12.5 g of 4-pyrrolidinobutyronitrile are run in over a period of 15 min, and the mixture is stirred for 2 hours while being allowed to return to room temperature. The reaction medium is cast onto 85 g of ice and 42.5 ml of 12N hydrochloric acid, the mixture is stirred for 1 hour and the aqueous phase is separated after settling has taken place, alkalinised with sodium hydroxide and extracted with ethyl ether.

The organic phase is washed with water, dried over drysodium sulphate and then treated with a solution of hydrogen chloride in isopropanol.

The precipitate obtained is purified by a crystallisation with CXA charcoal treatment in a 125:40 ethyl acetate/isopropanol mixture, to give 15 g of a water-soluble, beige powder.

M.P.$_{inst.}$ (Kofler)=124° C.
Yield=64.2%.

EXAMPLE 9

Preparation of 4-hexamethylenimino-1-(3-thienyl)-butanone hydrochloride (CRL 41725).

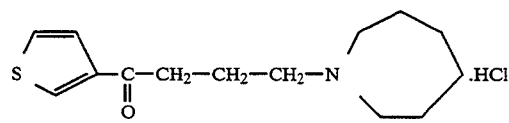

A solution of 16.3 g (0.10 mol) of 3-bromothiophene in 50 ml of ethyl ether is run, over a period of 15 min, into a solution, under a nitrogen atmosphere and maintained at −70° C., of 69 ml (0.11 mol) of a 1.6M hexane solution of butyllithium diluted in 150 ml of ethyl ether.

While the temperature is maintained at −50° C., 16.6 g (0.10 mol) of (hexamethylenimino)butyronitrile are run in over a period of 10 min, and the mixture is stirred for 4 hours while being allowed to return to room temperature. The reaction medium is cast onto 85 g of ice and 42.5 ml of 12N hydrochloric acid, the mixture is stirred for 1 hour and the aqueous phase is separated after settling has taken place, alkalinised with sodium hydroxide and extracted with ethyl ether.

The organic phase is washed with water, dried over dry sodium sulphate and then treated with a solution of hydrogen chloride in isopropanol.

The precipitate obtained is purified by a crystallisation with CXA charcoal treatment in absolute ethanol, to give 19.5 g of a water-soluble, slightly grey powder.

M.P.$_{inst.}$ (Kofler)=200°-202° C.
Yield=67.8%.

EXAMPLE 10

Preparation of 4-(3-methylpiperidino )-1-( 3thienyl)-butanone hydrochloride (CRL 41726).

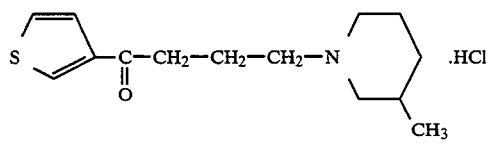

a) Preparation of 4-(3-methylpiperidino)butyronitrile.

27.2 g (0.25 mol) of 4-chlorobutyronitrile are run, over a period of 25 min, into a solution under reflux of 58.8 ml (0.50 mol) of 3-methylpiperidine in 65 ml of benzene. Refluxing is continued for 2 h, the precipitate is removed by filtration and the filtrate is taken to dryness under reduced pressure.

The residue is purified by a distillation under reduced pressure, to give 29.2 g of a colourless oil.

B.P.$_{5-6\ mm}$=100° C.
Yield=70.3%.

b) Preparation of 4-(3-methylpiperidino)-1-(3thienyl)-butanone.

A solution of 16.3 g (0.10 mol) of 3-bromothiophene in 50 ml of ethyl ether is run, over a period of 10 min, into a solution, under a nitrogen atmosphere and maintained at −70° C., of 69 ml (0.11 mol) of a 1.6M hexane solution of butyllithium diluted in 150 ml of ethyl ether.

While the temperature is maintained at −50° C., 16.6 g (0.10 mol) of the product obtained in a) are run in over a period of 15 min, and the mixture is stirred for 2 hours while being allowed to return to room temperature. The reaction medium is cast onto 85 g of ice and 42.5 ml of 12N hydrochloric acid, the mixture is stirred for 1 hour and the aqueous phase is separated after settling has taken place, alkalinised with sodium hydroxide and extracted with ethyl ether.

The organic phase is washed with water, dried over dry sodium sulphate and then treated with a solution of hydrogen chloride in isopropanol.

The precipitate obtained is purified by a crysallisation with CXA charcoal treatment in absolute ethanol, to give 16.1 g of a water-soluble, slightly pink powder.

M.P.$_{inst.}$ (Kofler)=184° C.
Yield=56%.
Total yield=39.4%

EXAMPLE 11

Preparation of 4-pyrrolidino-1-(2-thienyl)butanone 2,4,6-trimethoxybenzoate (CRL 41784)

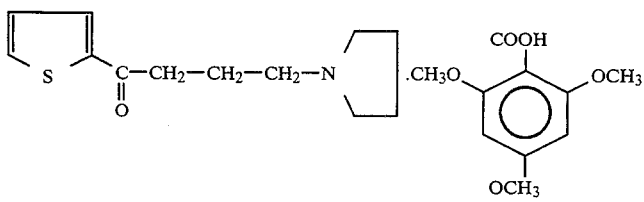

9.9 g (0.044 mol) of 4-pyrrolidino-1-(2-thienyl)butanone and 9.4 g (0.044 mol) of 2,4,6-trimethoxybenzoic acid are mixed in 50 ml of acetone. The mixture is stirred for 1 hour at room temperature and the reaction medium is diluted with 25 ml of acetone and brought to reflux to effect dissolution.

After cooling, 12.3 g of a beige powder are isolated by filtration, the product being soluble in water on heating.

M.P.$_{inst.}$ (Kofler) = 115° C.
Yield : 64.2%.

EXAMPLE 12

Preparation of 4-piperidino-1-(2-thienyl)butanone 2,4,6-trimethoxybenzoate (CRL 41777)

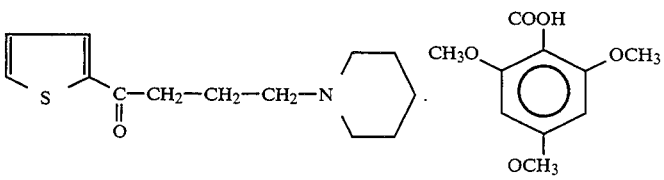

7.7 g (0.0356 mol) of 2,4,6-trimethoxybenzoic acid are introduced into a solution of 10 g (0.0365 mol) of 4-piperidino-1-(2-thienyl)butanone in 50 ml of methanol. The reaction medium is stirred for 30 min at room temperature and taken to dryness, and the residue is taken up with acetone. The product is rendered insoluble with ethyl ether and the precipitate isolated by filtration.

This product is purified by a wash in acetone and then by a crystallisation with CXA charcoal treatment in acetone, to give 6.8 g of a white powder which is soluble in water on heating.

M.p. = 100° C. (melts forming a paste)
Yield = 41.5%.

Pharmacological and toxicological results demonstrating the advantageous properties of the compounds according to the invention are given below.

a) Acute toxicity

The acute toxicity was determined orally in mice (NMRI).

| Compound | LD$_{50}$ (mg/kg) |
|---|---|
| Example 1 | 121 ± 10 |
| Example 2 | 235 ± 35 |
| Example 3 | 207 ± 29 |
| Example 7 | 131 ± 15 | b) Cardiovascular activity

The activity of the compounds administered intravenously was studied in anaesthetised dogs.

Compound of Example 1 (CRL 41687)

This compound significantly increases femoral flow rate at a dose of 1 mg/kg and above. At a dose of 4 mg/kg, it increases femoral flow rate by 170%.

For comparison, buflomedil at a dose of 4 mg/kg increases femoral flow rate by 106%.

In the same test, no significant change is observed in arterial blood pressure with the compound of Example 1, even at a dose of 4 mg/kg.

Compound of Example 2 (CRL 41696)

This compound significantly increases femoral flow rate at a dose of 1 mg/kg and above. At a dose of 2 mg/kg, it increases femoral flow rate with the same intensity as buflomedil at a dose of 4 mg/kg, without modifying arterial blood pressure. The effect of compound of Example 2 is longer-lasting than that of buflomedil.

Compound of Example 7 (CRL 41683)

This compound produces a significant and longlasting increase in femoral flow rate at a dose of 1.14 mg/kg and above. This increase is larger than that observed with buflomedil at a dose of 4 mg/kg.

c) Activity with respect to microcirculation

The activity of the compounds administered intravenously with respect to the microcirculation of the chamber of the rabbit's ear was studied.

At a dose of 1 mg/kg I.V., the compounds of Examples 1 and 7 (CRL 41687 and CRL 41683) produce a significant and long-lasting increase in non-terminal arteriolar diameter.

d) Action on metabolism

The effects of the compounds on the ATP in fresh blood were measured ex vivo by $^{31}$p NMR spectroscopy.

The results are given in the table below in the form of percentage changes.

| Compound | $\gamma$ATP | $\alpha$ATP | $\beta$ATP |
|---|---|---|---|
| Ex. 1 | +36.7% | +41.4% | +31.2% |
| Ex. 3 | +34.7% | +54.2% | +54.6% |

The same tests performed with buflomedil did not reveal any change in ATP level.

The subject of the present invention is also therapeutic compositions comprising as active principle a compound of formula I or one of its addition salts with pharmaceutically acceptable acids.

The therapeutic compositions according to the invention may be administered to man or animals orally or parenterally.

They can be in the form of solid, semi-solid or liquid preparations. As an example, there may be mentioned tablets, hard gelatin capsules, suppositories and injectable solutions or suspensions, as well as retard forms and slow-release implanted forms.

In these compositions, the active principle is generally mixed with one or more common pharmaceutically acceptable excipients well known to those skilled in the art.

The quantity of active principle administered naturally depends on the patient undergoing treatment, the administration route and the severity of the disease.

In general, the compounds according to the invention may be administered orally at a dose of 100 to 800 mg/day.

I claim:

1. A compound of the formula:

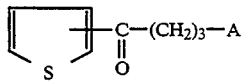 (I)

in which A is pyrrolidino or pyrrolidino having 1 or 2 substituents selected from the group consisting of $C_1$-$C_3$ alkyl and $C_1$-$C_3$ hydroxyalkyl, or a pharmaceutically acceptable acid-addition salt thereof.

2. The compound of claim 1 wherein A is pyrrolidino.

3. The compound of claim 1 that is 4-pyrrolidino-1-(2thienyl)butanone or a pharmaceutically acceptable acid-addition salt thereof.

4. A therapeutic composition having vasodilator activity comprising an effective amount of the compound of claim 1 in admixture with a pharmaceutically acceptable carrier.

5. The therapeutic composition of claim 4, wherein A is pyrrolidino.

6. The therapeutic composition of claim 4, wherein the compound is 4-pyrrolidino-1-(2-thienyl)butanone or a pharmaceutically acceptable acid-addition salt thereof.

7. A method for treating a circulation disorder, which comprises administering to a human in need thereof a compound of the formula:

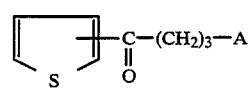 (I)

in which A is pyrrolidino or pyrrolidino having 1 or 2 substituents selected from the group consisting of $C_1$-$C_3$ alkyl or $C_1$-$C_3$ hydroxyalkyl groups, or a pharmaceutically acceptable acid-addition salt thereof.

8. The method of claim 7 wherein the compound is 4-pyrrolidino-1-(2-thienyl) butanone or a pharmaceutically acceptable acid-addition salt thereof.

* * * * *